United States Patent
Villa et al.

(10) Patent No.: US 6,239,301 B1
(45) Date of Patent: May 29, 2001

(54) PROCESS FOR THE REMOVAL OF HEAVY METALS

(75) Inventors: Marco Villa, Milan; Vincenzo Cannata, Sasso Marconi; Alessandro Rosi, Borgo San Lorenzo; Pietro Allegrini, Lonigo, all of (IT)

(73) Assignee: Zambon Group S.p.A., Vicenza (IT)

( * ) Notice: Subject to any disclaimer, the term of this patent is extended or adjusted under 35 U.S.C. 154(b) by 0 days.

(21) Appl. No.: 09/423,315

(22) PCT Filed: May 4, 1998

(86) PCT No.: PCT/EP98/02628

§ 371 Date: Dec. 30, 1999

§ 102(e) Date: Dec. 30, 1999

(87) PCT Pub. No.: WO98/51646

PCT Pub. Date: Nov. 19, 1998

(30) Foreign Application Priority Data

May 13, 1997 (IT) .............................. MI97A1108

(51) Int. Cl.[7] .............................. C07F 15/00; C02F 1/42; B01D 21/01

(52) U.S. Cl. .......................... 556/136; 556/137; 210/688; 210/735

(58) Field of Search .................................. 556/136, 137; 210/688, 735

(56) References Cited

U.S. PATENT DOCUMENTS

| 5,412,143 | 5/1995 | Giordano et al. ..................... 558/298 |
| 5,427,247 | 6/1995 | Dugan et al. ............................ 209/5 |
| 5,760,220 | 6/1998 | Giguere et al. ....................... 540/521 |

FOREIGN PATENT DOCUMENTS 2-009890   1/1990   (JP) .

*Primary Examiner*—Porfirio Nazario-Gonzalez
(74) *Attorney, Agent, or Firm*—Arent Fox Kintner Plotkin Kahn PLLC

(57) ABSTRACT

A method for the removal of heavy metals from solutions of organic compounds by treatment with cysteine or with an N-acylcysteine is described. Organic compounds with a content of heavy metal, for example palladium, particularly low and suitable for the preparation of compounds with pharmacologic activity can be isolated from the resultant solutions.

10 Claims, No Drawings

PROCESS FOR THE REMOVAL OF HEAVY METALS

The present invention relates to a process for the removal of heavy metals from organic compounds by treatment with cysteine or N-acylcysteine and, more particularly, it relates to a process for the removal of heavy metals from solutions of organic compounds in solvents immiscible with water, The heavy metals, more commonly palladium and nickel, are widely used in industrial synthetic processes for the preparation of compounds useful in different fields.

Because of the easy formation of complexes, a very common drawback bound to the use of these heavy metals is that they often remain present in relevant amounts in the organic compounds.

This results in a decrease of the compound purity and in the consequent need of removing the heavy metals from the compound.

The need of removing the heavy metals has a particular importance when the compound containing the high amount of metals is a pharmacologically active compound or an intermediate for the preparation of a pharmacologically active compound.

In fact for pharmaceutically useful compounds the content of heavy metals must be particularly low not only for reasons of purity of the compound but also for obvious reasons of therapeutical safety.

The relevance of the problem of the impurity of heavy metals, in particular of palladium, in the chemical-pharmaceutical industry is well underlined by Maryanoff C. A. et al. in chapter 18 entitled "Catalysis from the Perspective of an Organic Chemist: Common Problems and Possible Solutions" published in the book Chemistry & Industry (Dekker) 1988, 33(Catal. Org. React.) 359–79.

For example, by citing the synthesis of the compound known as McN-5691. the Authors report several attempts carried out in order to remove the high content of palladium (table III on page 374). The results were negative and the problem was resolved only with a complete change of the synthetic scheme (FIG. 14 on page 376).

We have now found that also relevant amounts of heavy metals can be simply and efficiently removed from organic compounds by treating solutions of these organic compounds with cysteine or with a N-acylcysteine.

Therefore, object of the present invention is a process for the removal of heavy metals from organic compounds characterised in that a solution of the organic compound in a solvent immiscible with water is treated with a cysteine derivative of formula

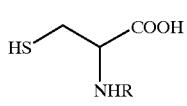

(I)

wherein
R is a hydrogen atom, a linear or branched $C_{1-C6}$ acyl group or a benzoyl group.

The process object of the present invention is of easy industrial applicability and allows to efficiently remove the heavy metals and in particular palladium.

The compounds of formula I are known or they can be easy prepared by known methods, specific examples including cysteine N-acetylcysteine, N-benzoylcysteine, N-pivaloylcysteine and N-propionylcysteine.

Preferably, cysteine or N-acetylcysteine (NAC), still more preferably N-acetylcysteine, are used in the process of the present invention.

The amount of cysteine derivative of formula I to be used depends on the amount of heavy metal to be removed but it is at least equimolar with respect to the heavy metal.

In general a molar amount of compound I from 1:1 to 100:1 with respect to the content of heavy metal is used.

Preferably a molar ratio compound I:heavy metal from 5:1 to 15:1 is used.

The organic compound containing the impurity of the heavy metal must be dissolved in a solvent immiscible with water or in a mixture of solvents of which at least one is immiscible with water.

The selection of the suitable organic solvent or of the mixture of solvents depends exclusively on the solubility characteristics of the compound to be purified.

Examples of these solvents are toluene, xylene, methylene chloride, chlorobenzene, 1.2-dichlorobenzene and aliphatic hydrocarbons such as hexane, optionally in admixture with aprotic dipolar solvents such as dimethylsulphoxide, tetrahydrofuran and acetonitrile.

The compound of formula I can be used as such, that is as a powder, or more preferably dissolved in water, that is as an aqueous solution.

When used as a powder, the removal of the heavy metals is carried out by filtration.

When used as an aqueous solution, the concentration of the aqueous solution of the compound of formula I is generally between 5% and 70% w/w.

From a practical viewpoint, the use of concentrated solutions, preferably with concentrations between 20% and 60% w/w. is preferred.

The aqueous solution of the compound of formula I can be prepared separately so carrying out the treatment for the removal of the heavy metals by washing the solution containing the organic compound with the aqueous solution of compound I.

Alternatively, the suitable amount of compound of formula I and the necessary amount of water can be added separately to the solution of the organic compound to be purified.

When the organic compound is dissolved in a mixture of solvents including water, the removal treatment can be simply carried out by adding the suitable amount of compound of formula I directly to the solution of the organic compound.

By separation of the phases, the heavy metal remains in the aqueous phase, likely in the form of a complex with the compound of formula I, while tie organic compound remains in solution in the organic phase.

The treatment time can be variable but generally an increase of the amount of removed heavy metal is observed when the treatment time is increased.

In the same manner, the treatment time and the molar ratio of compound I remaining the same, an increase of the amount of removed heavy metal is observed when the treatment temperature is increased.

In general, the process for the removal of the heavy metals according to the present invention is carried out at a temperature between the room value and the reflux temperature of the mixture, preferably between 20° C. and 60° C.

Depending on their initial content, the desired low values of the heavy metals can be reached after one treatment or after more treatments according to the process object of the present invention.

Furthermore, we have found that the efficacy of the treatment for the removal of the heavy metals according to the process object of the present invention can be further increased by carrying out a final washing with an aqueous basic solution.

Suitable basic solutions are aqueous solutions of ammonia, aqueous solutions of amines, such as triethylamine, and aqueous solutions of inorganic bases such as sodium or potassium carbonates, bicarbonates and hydroxides.

Preferably an aqueous 30% ammonia solution, which is directly added at the end of the treatment with the aqueous solution of compound I, that is before the separation of the phases, is used.

As already underlined, the process object of the present invention is useful for the removal of several heavy metals which are commonly used as reagents such as tin, palladium and other metals which can be retained as impurities in the form of complexes with organic compounds.

A preferred embodiment of the process object of the present invention is the removal of palladium.

In fact palladium is widely used in the organic synthesis processes especially as catalyst.

For a general reference to the use of palladium see, for example, Jiro Tsuji. Palladium Reagents and Catalysts, John Wiley & Sons (1995).

As already underlined, palladium is also the heavy metal which more frequently remains as impurity of difficult removal in the organic compounds.

The preferred method for the removal of palladium by treatment with an aqueous solution of N-acetylcysteine is extremely versatile and applicable to several organic compounds.

For example, the method object of the present invention proved to be particularly efficient in the removal of high amounts of palladium present in heteroarylphenylalanines prepared by, coupling a phenylalanine derivative with a heteroaryl-zinc halide in the presence of a palladium(0) based catalyst (international patent applications no. PCT/EP97/07024 and no. PCT/EP98/00126 in the name of the present Applicant, filed on Dec. 12. 1997 and on Jan. 12, 1998 respectively).

The process object of the present invention proved to be equally efficient in the removal of palladium, present as an impurity, from intermediates for the synthesis of diflunisal and from intermediates for the synthesis of 5,8-dihydro-2, 4-dimethyl-8-[(2'-(1H-tetrazol-5-yl)[1,1'-biphenyl]-4-yl] methyl]pyrido[2,3-d]pyrimidin-7(6H)-one prepared by coupling reaction in the presence of palladium(0)based catalysts according to the processes described in the European patent application 0 494 419 (Zambon Group S.p.A.) and in the patent application WO 96/40684 (American Home Products Corporation), respectively.

A particularly preferred embodiment of the process object of the present invention is the following.

A solution of the organic compound containing palladium is heated to a temperature between 20 and 60° C. and an aqueous solution of N-acetylcysteine is added to.

After some hours, the mixture is cooled to room temperature and a 30% ammonia solution is added by keeping under stirring for some minutes.

The phases are separated and the purified compound is isolated from the organic phase.

In order to better illustrate the present invention the following examples are now given.

For the determination of the residual palladium the method of atomic absorption was used, calculating the palladium content as ppm with respect to the organic compound.

EXAMPLE 1

Bromoethane (1.33 g. 0.0122 moles) was added to a mixture of tetrahydrofuran (18.2 ml), toluene (18.2 ml) and magnesium (1.76 g; 0.0724 moles). The temperature arose up to 60° C. and the mixture was cooled to 35° C. and added with 2-bromothiazole (10 g, 0.061 moles) in 1.5 hours.

The mixture was kept under stirring for 1 hour, cooled and added to a suspension of anhydrous zinc chloride (16.4 g. 0.12 moles) in tetrahydrofuran (36.4 ml), keeping the temperature below 40° C.

The mixture was kept under stirring for 1 hour, then heated to 50° C. and N-(tert-butoxycarbonyl)-4-iodo-L-phenylalanine methyl ester (19.1 g. 0.047 moles) and, subsequently, palladium acetate (0.15 g; 0.67 mmoles) and triphenylphosphine (0.36 g 1.37 mmoles) were added.

The mixture was kept under stirring for 1.5 hours the suspension was cooled to 30° C. and poured into water (45 ml), toluene (30 ml) and 2N hydrochloric acid (10 ml).

The phases were separated and the organic phase (containing 3400 ppm palladium) was washed with water (20 ml) and added with a solution of N-acetylcysteine (5 g) and water (20 ml). The suspension was kept under stirring at 50° C. for 1 hour.

After cooling at 25° C., ammonia 28% (25 ml) was added. The phases were separated (the residual content of palladium was 800 ppm).

The washing with N-acetylcysteine and ammonia was repeated.

The organic phase was brought to residue under vacuum. The palladium content in the residue was 550 ppm.

EXAMPLE 2

A mixture of tetrahydrofuran (11 ml), toluene (5 ml) and zinc (1.56 g; 0.0238 moles) was heated under reflux and added with 2-bromothiazole (3.6 g: 0.022 moles) in about 1.5 hours.

The mixture was kept under stirring under reflux for 1 hour and cooled at 50° C. N-formyl-4-iodo-L-phenylalanine methyl ester (5.8 g; 0.0174 moles) and, subsequently, palladium acetate (0.035 g, 0.15 mmoles) and triphenylphosphine (0.092 g 0.35 mmoles) were added.

The mixture was kept under stirring for 1 hour, the suspension was cooled at 30° C. and poured into water (10 ml). Acetic acid (0.5 ml) was added and the phases were separated.

The organic phase was brought to residue under vacuum and the residue (containing 3290 ppm palladium) was taken with methylene chloride (25 ml). A solution of N-acetylcysteine (0.8 g) in water (1.8 ml) was added. The suspension was kept under stirring at 30° C. for 1 hour.

After cooling to 25° C., ammonia 28% (3 ml) and water (10 ml) were added. The phases were separated and the washing with N-acetylcysteine and ammonia was repeated (the residual content of palladium was 1100 ppm). A third washing with N-acetylcysteine was repeated and the organic phase was brought to residue under vacuum. The palladium content in the residue was 360 ppm.

EXAMPLE 3

In a 250 cc reactor with external jacket, thermometer, reflux condenser and mechanical stirrer, kept under nitrogen atmosphere, crystallised 8-[2'-(3-tert-butyl-2H-tetrazol-5-yl)-biphenyl-4-ylmethyl]-2,4-dimethyl-5,8-dihydro-6H-pyrido[2,3-d]-pyrimidin-7-one (20.0 g. 0.0428 moles: Pd content=777 ppm) and toluene (87.1 g) were charged.

The resultant solution was brought to 40° C. under stirring. A solution prepared with N-acetylcysteine (1.2 g, 7.36 mmoles) and water (10.0 g) was added.

After 24 hours the reaction mixture was cooled to room temperature and 30% ammonia (4.0 g) was added.

The mixture was kept under stirring for 30 minutes before separating the phases.

The Pd content was evaluated in the toluene phase with the following result: Pd<16 ppm.

EXAMPLE 4

The procedure described in example 3 was repeated but substituting N-acetylcysteine with cysteine.

The Pd content was brought from the initial content of 777 ppm to a value of 31 ppm.

EXAMPLE 5

In a 2 l reactor with external jacket, valve at the bottom, thermometer, reflux condenser and mechanical stirrer, an organic solution containing 8-[2'-(3-tert-butyl-2H-tetrazol-5-yl)-biphenyl-4-ylmethyl]-2,4-dimethyl-5,8-dihydro-6H-pyrido[2,3-d]-pyrimidin-7-one at 18% (20.0 g. 0.0428 moles; Pd content=777 ppm) in a mixture of toluene and tetrahydrofuran (1240 g corresponding to 0.477 moles of organic compound, Pd content 3700 ppm) was charged at room temperature and under nitrogen atmosphere.

The internal temperature was brought to 60° C. and, under stirring. N-acetylcysteine (15.7 g. 0.0962 moles) and water (8.0 g) were added.

The mixture was kept under stirring at 60° C. for 8 hours, then was cooled to 35–40° C. and water (48.7 g) and 30% ammonia (56.7 g; 0.99 moles) were added.

The mixture was kept under stirring for 30 minutes at 40° C. then the stirring was stopped and the mixture kept at rest for 15 minutes.

By working at 40° C. the phases were separated and the palladium content was evaluated directly from the organic solution (390 ppm).

EXAMPLE 6

In an anhydrous 250 cc reactor, magnesium turnings (9.9 g. 0.406 moles), tetrahydrofuran (60 g) and toluene (60 g) were charged under nitrogen flux.

The mixture was heated at 70° C. 4-Bromoanisole (7.5 g. 0.04 moles) and, subsequently, 1,2-dibromoethane (0.3 g. 0.0016 moles) were added to the mixture.

After 15 minutes an increase of the internal temperature up to 83° C., gas evolution and appearance of a green colour in the reaction mixture were observed.

Then, further 4-bromoanisole (67.4 g; total 0.36 moles) was slowly added keeping the temperature between 70 and 75° C. At the end of the addition the reaction mixture was kept under stirring at 74° C. for 5 hours. At the end of this period the solution containing the Grignard compound was filtered.

In the meantime, in a 500 ml reactor 2,4-difluoro-bromobenzene (73.4 g, 0.380 moles), palladium acetate (0.256 g. 0.0014 moles) and triphenylphosphine (1.2 g: 0.00457 moles) were charged under nitrogen flux.

After heating to 90° C. and keeping the reaction mixture under stirring, the solution containing the Grignard compound was added dropwise in 4 hours.

During the addition the internal temperature was kept below 107° C.

At the end of the addition the reaction mixture was kept under stirring at 95° C. for further 5 hours, then cooled to 85° C. and water (80 g) was added by contemporaneously distilling off tetrahydrofuran.

The reaction mixture was acidified with 37% hydrochloric acid (4.1 g) before carrying out the separation of the phases.

The organic phase (152 g) was divided out, after dilution with toluene (100.0 g), into two portions of 125 g each, a portion was treated with N-acetylcysteine (1.12 g) and water (0.60 g) at 60° C. for 8 hours while the other portion is treated with water (0.60 g) at 60° C. for 8 hours in order to obtain comparative data.

At the end of the treatment, the two different portions were cooled at 40° C. and washed with 15% ammonia (8 g).

The organic solution treated with N-acetylcysteine had a palladium content equal to 50 ppm (3.5% of the initial content) while the comparative solution had a palladium content equal to 965 ppm (68.9% of the initial content).

What is claimed is:

1. A process for the removal of palladium from organic compounds characterised in that a solution of the organic compound in a solvent immiscible with water is treated with a cysteine derivative of formula

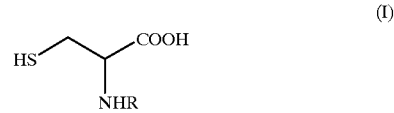

(I)

wherein

R is a hydrogen atom, a linear or branched $C_1$–$C_6$ acyl group or a benzoyl group.

2. A process according to claim 1 wherein the molar amount of compound I is from 1:1 to 100:1 with respect to the content of palladium.

3. A process according to claim 2 wherein the molar ratio is between 5:1 and 15:1.

4. A process according to claim 1 wherein N-acetylcysteine is used.

5. A process according to claim 1 wherein an aqueous solution of the compound of formula I is used.

6. A process according to claim 5 wherein the concentration of the aqueous solution is between 5% and 70% w/w.

7. A process according to claim 1 wherein the solvent is selected among toluene, xylene, methylene chloride, chlorobenzene, 1,2-dichlorobenzene and aliphatic hydrocarbons optionally in admixture with aprotic dipolar solvents.

8. A process according to claim 1 further comprising the treatment with a basic aqueous solution.

9. A process according to claim 8 wherein the basic aqueous solution is an ammonia aqueous solution.

10. A process for the removal of palladium from organic compounds characterised in that a solution of the organic compound in a solvent immiscible with water is first treated with an aqueous solution of N-acetylcysteine and then with an ammonia aqueous solution.

* * * * *